US011504395B2

(12) United States Patent
Váradi et al.

(10) Patent No.: US 11,504,395 B2
(45) Date of Patent: Nov. 22, 2022

(54) ORAL PYROPHOSPHATE FOR USE IN REDUCING TISSUE CALCIFICATION

(71) Applicant: Stichting Het Nederlands Kanker Instituut-Antoni van Leeuwenhoek Ziekenhuis, Amsterdam (NL)

(72) Inventors: András Váradi, Budapest (HU); Dóra Dedinszki, Budapest (HU); Flóra Mária Szeri, Budapest (HU); Piet Borst, Amsterdam (NL); Jan Koenraad Van De Wetering, Amsterdam (NL)

(73) Assignee: Stichting Het Nederlands Kanker Instituut-Antoni van Leeuwenhoek Ziekenhuis, Amsterdam (NL)

( * ) Notice: Subject to any disclaimer, the term of this patent is extended or adjusted under 35 U.S.C. 154(b) by 161 days.

(21) Appl. No.: 16/333,856

(22) PCT Filed: Sep. 13, 2017

(86) PCT No.: PCT/NL2017/050601
§ 371 (c)(1),
(2) Date: Mar. 15, 2019

(87) PCT Pub. No.: WO2018/052290
PCT Pub. Date: Mar. 22, 2018

(65) Prior Publication Data
US 2019/0216850 A1 Jul. 18, 2019

(30) Foreign Application Priority Data

Sep. 15, 2016 (NL) .................................. 2017471

(51) Int. Cl.
*A61K 33/42* (2006.01)
*A61P 9/00* (2006.01)
*A61K 9/00* (2006.01)

(52) U.S. Cl.
CPC ............ *A61K 33/42* (2013.01); *A61K 9/0053* (2013.01); *A61P 9/00* (2018.01)

(58) Field of Classification Search
None
See application file for complete search history.

(56) References Cited

U.S. PATENT DOCUMENTS

| 4,806,342 A * | 2/1989 | Gaffar | A61K 8/24 |
| | | | 424/49 |
| 5,686,114 A * | 11/1997 | Welsh | A61K 33/42 |
| | | | 424/601 |
| 6,780,436 B1 * | 8/2004 | Lopez-Cabrera | A61K 31/444 |
| | | | 424/490 |
| 2009/0022795 A1 * | 1/2009 | Ghosh | A61P 1/04 |
| | | | 424/465 |
| 2011/0262555 A1 | 10/2011 | Riser et al. | |

FOREIGN PATENT DOCUMENTS

WO         01/49295         7/2001

OTHER PUBLICATIONS

Li et al. Cell Cycle 2015 14(7):1082-1089 (Year: 2015).*
Li et al. Journal of Investigative Dermatology 2016 136:50-556 (Year: 2016).*
Dabisch-Ruthe et al. Kidney International 2011 79:512-517 (Year: 2011).*
Finger et al. Survey of Ophthalmology 2009 54(2):272-285 (Year: 2009).*
Dabisch-Ruthe et al. Journal of Dermatological Science 2014 2014 75:109-120 (Year: 2014).*
Nitschke et al. Frontiers in Genetics 2012 3:302:1-3 (Year: 2012).*
Rutsch et al. Circulation:Cardiovascular Genetics 2008 1:133-140 (Year: 2008).*
Uitto et al. Expert Opinion in Orphan Drugs 2014 2(6):567-577— citations of online publication p. 1-20 (Year: 2014).*
O'Neill et al. Kidney International 2011 79:512-517 (Year: 2011).*

(Continued)

*Primary Examiner* — Melissa S Mercier
*Assistant Examiner* — Caralynne E Helm
(74) *Attorney, Agent, or Firm* — Casimir Jones, S.C.; Robert A. Goetz

(57) ABSTRACT

The invention is concerned with use of oral inorganic pyrophosphate for preventing and/or reducing tissue calcification, particularly soft tissue calcification, and/or diseases or disorders characterized by low plasma PPi levels, as, e.g., occurs in chronic kidney disease (CKD), end-stage renal disease (ESRD), generalized arterial calcification of infancy (GACI), Pseudoxanthoma elasticum (PXE), Arterial Calcification Due to Deficiency of CD73 (ACDC), Ehlers-Danlos syndrome, arteriosclerosis obliterans, venous calcifications, crystal deposition disorders, calcification resulting from neurological disorders, calcinosis universalis, calcinosis circumscripta, scleroderma, dermatomyositis, systemic lupus erythematosus, hyperparathyroidism, neoplasms, milk-alkali syndrome, hypervitaminosis D, tumoral calcinosis, hypophosphatemic rickets, ossification of the posterior longitudinal ligament of the spine, myocardial ischemia, joint calcification, heterotropic ossification of traumatized muscle, angioid streaks, diabetes mellitus type II, cardiovascular disorder, or atherosclerosis.

4 Claims, 5 Drawing Sheets

(56) References Cited

OTHER PUBLICATIONS

Russell et al. Arthritis and Rheumatism 1976 19(3):465-478 (Year: 1976).*
Dedinski et al. EMBO Molecular Medicine 2017 9:1463-1470 (Year: 2017).*
Orriss, Isabel et al. "Pyrophosphate: a key inhibitor of mineralisation" Current Opinion in Pharmacology, Elsevier Science Publishers, NL, vol. 28, Apr. 7, 2016, pp. 57-68.
O'Neill, W. Charles et al. "Treatment with pyrophosphate inhibits uremic vascular calcification" Kidney International, vol. 79, No. 5, Dec. 1, 2010, pp. 512-517.
International Search Report, International Patent Application No. PCT/NL2017/050601, dated Jan. 5, 2018, 4 pages.

\* cited by examiner

ORAL PYROPHOSPHATE FOR USE IN REDUCING TISSUE CALCIFICATION

FIELD OF THE INVENTION

The present invention is in the field of tissue calcification, more particularly soft tissue calcification, as well as other diseases or disorders characterized by low inorganic pyrophosphate blood levels.

BACKGROUND OF THE INVENTION

Physiological mineralization is essential for the normal development of vertebrates. It is restricted to specific sites of the body. In mammals, biominerals predominantly consist of calcium and phosphate, together forming hydroxyapatite. In plasma and several other body fluids calcium and phosphate are present at concentrations that by far exceed their solubility constant ($1 \times 10^{-26}$). Vertebrates have evolved mechanisms to stabilize this supersaturated solution and to allow the regulated precipitation of calcium and phosphate only at specific bodily compartments.

Calcification (deposits of calcium phosphate) may occur in many different soft tissues in a variety of local and systemic (throughout the body) conditions. Calcium phosphate crystals have a remarkable tendency to aggregate into snowball-like clumps and are invariably associated with particular collagens. Collagens are fibrous, insoluble proteins found in the connective tissues, including skin, ligaments, and cartilage. Collagen represents about 30 percent of the total body protein.

Pyrophosphate (PPi) is a central factor in prevention of precipitation of calcium and phosphate in soft peripheral tissues. The liver is the most important source of circulatory PPi, via a pathway depending on ABCC6-mediated ATP release. Outside the hepatocytes, but still within the liver vasculature, released ATP is rapidly converted into AMP and PPi by the ectoenzyme ectonucleotide pyrophosphatase phosphodiesterase 1 (ENPP1). Pyrophosphate is a potent inhibitor of hydroxyapatite formation, and, under normal conditions, functions to inhibit soft tissue calcification, e.g., vascular calcification.

Inactivating mutations in the genes encoding the enzymes involved in PPi homeostasis result in rare hereditary calcification disorders. For example, absence of functional ABCC6 results in pseudoxanthoma elasticum (PXE), a late onset ectopic calcification disorder, with lesions found in the skin, eyes and cardiovascular system. Biallelic inactivating mutations in ENPP1 cause arterial calcification and generalized calcification of infancy (GACI), a condition that can become life-threatening shortly after birth due to massive calcification of the large and medium-sized arteries. GACI patients have virtually no PPi in their blood, which explains the severity of the disease.

As reduced PPi concentrations in the circulation underlie the ectopic calcification disorders PXE and GACI, an obvious treatment for these disorders as well as other disorders characterized by reduced PPi concentrations in the circulation would be PPi supplementation. Due to the necessity to, in some instances, treat patients life-long and the short half-life of PPi, oral administration would be preferred for such a treatment. However, it has long been thought, and is therefore a reigning dogma, that PPi is ineffective when given orally (H. Fleisch, et al., Calc. Tiss. Res. 2, Suppl. (1968) 10; Francis, et al. Science (1969), 165(3899), 1264-1266; Orriss, I R., et al. Curr Opin Pharmacol. (2016) 28, 57-68).

SUMMARY OF THE INVENTION

In a first aspect, the present disclosure relates to inorganic pyrophosphate (PPi) for use in preventing and/or treating diseases or disorders characterized by tissue calcification, particularly soft tissue calcification, or diseases or disorders characterized by low plasma PPi levels, wherein said inorganic pyrophosphate is administered in oral form.

The soft tissue calcification may be vascular calcification such as arterial calcification or intimal calcification. The tissue calcification may be in a subject having ENPP1 deficiency, chronic kidney disease (CKD), end-stage renal disease (ESRD), generalized arterial calcification of infancy (GACI), Pseudoxanthoma elasticum (PXE), Arterial Calcification Due to Deficiency of CD73 (ACDC), Ehlers-Danlos syndrome, arteriosclerosis obliterans, venous calcifications, crystal deposition disorders, calcification resulting from neurological disorders, calcinosis universalis, calcinosis circumscripta, scleroderma, dermatomyositis, systemic lupus erythematosus, hyperparathyroidism, neoplasms, milk-alkali syndrome, hypervitaminosis D, tumoral calcinosis, hypophosphatemic rickets, ossification of the posterior longitudinal ligament of the spine, myocardial ischemia, joint calcification, heterotropic ossification of traumatized muscle, angioid streaks, diabetes mellitus type II, cardiovascular disorder, or atherosclerosis.

The inorganic pyrophosphate may advantageously be administered to a human subject. The inorganic pyrophosphate may be administered daily.

In a second aspect, the present disclosure provides a method for preventing and/or reducing tissue, particularly soft tissue, calcification, and/or diseases or disorders characterized by low plasma PPi levels comprising the step of: administering to a subject in need thereof a therapeutically effective amount of inorganic pyrophosphate, wherein said inorganic pyrophosphate is administered in oral form.

The soft tissue calcification may be vascular calcification such as arterial calcification or intimal calcification.

The inorganic pyrophosphate may be sufficient to achieve a transient increase in plasma PPi level in the subject.

The transient increase in plasma PPi level is characterized by a PPi level that is at least about 40% of the plasma PPi level in a healthy subject.

The transient increase in plasma PPi level may be maintained for at least about 15 minutes.

The subject may have a disease or disorder characterized by low plasma PPi levels, e.g., chronic kidney disease (CKD), end-stage renal disease (ESRD), generalized arterial calcification of infancy (GACI), Pseudoxanthoma elasticum (PXE), Arterial Calcification Due to Deficiency of CD73 (ACDC), Ehlers-Danlos syndrome, arteriosclerosis obliterans, venous calcifications, crystal deposition disorders, calcification resulting from neurological disorders, calcinosis universalis, calcinosis circumscripta, scleroderma, dermatomyositis, systemic lupus erythematosus, hyperparathyroidism, neoplasms, milk-alkali syndrome, hypervitaminosis D, tumoral calcinosis, hypophosphatemic rickets, ossification of the posterior longitudinal ligament of the spine, myocardial ischemia, joint calcification, heterotropic ossification of traumatized muscle, angioid streaks, diabetes mellitus type II, cardiovascular disorder, or atherosclerosis.

In an embodiment, the subject has GACI or PXE.

DETAILED DESCRIPTION OF THE INVENTION

Definitions

Unless defined otherwise, all technical and scientific terms used herein have the same meaning as commonly understood by one of ordinary skill in the art to which this invention belongs.

As used herein, the term "subject" includes both mammals and non-mammals. Examples of mammals include, but are not limited to, humans, chimpanzees, apes, monkeys, cattle, horses, sheep, goats, swine, rabbits, dogs, cats, rats, mice, guinea pigs, and so on. Examples of non-mammals include, without limitation, birds, fish, and the like.

As used herein, the term "therapeutically effective amount" refers to a non-toxic amount of PPi that is sufficient to result in improved treatment or healing of a disease or disorder, or a decrease in the rate of advancement of a disease or disorder.

The term "soft tissue" as used herein refers to the tissues that connect, support, or surround other structures and organs of the body, not being hard tissue such as bone. Soft tissue includes tendons, ligaments, fascia, skin, fibrous tissues, fat, and synovial membranes (which are connective tissue), and muscles, nerves and blood vessels (which are not connective tissue).

The term "about" as used herein is meant to denote variations of ±20% or ±10%, or ±5% or ±1% from the specified value, as such variations are still suitable to perform the methods taught herein.

The term "treating" as used herein refers to the administration of PPi to a subject who has a disease or disorder characterized by low PPi levels in the blood, or other progressive disorder characterized by the accumulation of deposits of calcium and other minerals, with the purpose of curing, healing, alleviating, relieving, altering, remedying, ameliorating, preventing, improving, or affecting the disease or disorder. The term "treating" refers to any indicia of success in the treatment or amelioration of an injury, pathology or condition, including any objective or subjective parameter such as abatement; remission; diminishing of symptoms; increasing tolerability of the injury, pathology or condition; slowing progression of the injury, pathology or condition; slowing the rate of degeneration or decline; or improving the subject's physical or mental well-being. Treatment may be therapeutic or prophylactic.

The term "preventing and/or reducing" as used herein refers to the prevention of calcification, the prevention of further calcification in (soft) tissues that already contain some degree of calcification as well as (partial) reversal of calcification already formed.

Methods of Treatment

The present invention relates to use of orally administered inorganic pyrophosphate for treatment of tissue calcification, particularly in soft tissue calcification, e.g., vascular calcification. It was surprisingly found that, despite the reigning, over 50 year old, dogma that pyrophosphate has to be injected as it is ineffective orally because of hydrolytic destruction within the gut (Orriss et al. 2016, supra), oral PPi administration attenuated calcification in mouse models of pseudoxanthoma elasticum (PXE) and generalized arterial calcification of infancy (GACI). Remarkably, the effect was maximal in pups of GACI mice if PPi was administered during pregnancy. Moreover, PPi uptake from the oral cavity and from the stomach was detected showing that PPi is not only absorbed from the gut but also from the oral cavity and stomach. Hence, the present inventors have proven that orally administered inorganic pyrophosphate can reach the blood circulation and counteract soft tissue calcification, making long-term treatment of soft tissue calcification disorders and diseases, some of which are hereditary and require life-long treatment, feasible.

In an aspect, the present invention provides the use of PPi, wherein the PPi is to be administered in oral form, for use as a medicament, in particular for preventing and/or treating diseases or disorders characterized by tissue calcification, particularly soft tissue calcification, and/or diseases or disorders characterized by low plasma PPi levels.

Thus, the present invention provides the use of inorganic pyrophosphate for treating diseases or disorders characterized by tissue calcification, particularly soft tissue calcification, wherein said inorganic pyrophosphate is administered in oral form. The invention also provides a method for reducing tissue calcification, particularly soft tissue calcification, comprising the step of administering to a subject in need thereof inorganic pyrophosphate, wherein said inorganic pyrophosphate is administered in oral form.

The risk of oral PPi to patients is probably negligible. The WHO considers PPi a nontoxic physiological metabolite with a high maximal tolerable daily intake value (MTDI). Moreover, it is used generally in the food industry as an additive, and its Code for Federal Regulation by the FDA states: "This substance is generally recognized as safe when used in accordance with good manufacturing practice."

The subject to be treated may be a human patient exhibiting low levels of pyrophosphate, suffering from a disease or disorder associated with low levels of pyrophosphate, or suffering from a progressive disorder characterized by the accumulation of deposits of calcium and other minerals (mineralization) in elastic fibers. Mineralization may occur at the heart, arteries, blood vessels, kidney, spine ligaments, skin, eyes, or the digestive tract. The subject may be of any age and gender, and may have low plasma PPi. Low plasma PPi may be caused by, for example, congenital deficiencies as taught herein above or others known to result in low plasma PPi levels. Low plasma PPi is also frequently seen in subjects with chronic kidney disease, end-stage renal disease/failure, diabetes mellitus and other conditions. Accordingly, the subject in need of therapy may have ENPP1 deficiency, chronic kidney disease (CKD), end-stage renal disease (ESRD), generalized arterial calcification of infancy (GACI), Pseudoxanthoma elasticum (PXE), Arterial Calcification Due to Deficiency of CD73 (ACDC), Ehlers-Danlos syndrome, arteriosclerosis obliterans, venous calcifications, crystal deposition disorders, calcification resulting from neurological disorders, calcinosis universalis, calcinosis circumscripta, scleroderma, dermatomyositis, systemic lupus erythematosus, hyperparathyroidism, neoplasms, milk-alkali syndrome, hypervitaminosis D, tumoral calcinosis, hypophosphatemic rickets, ossification of the posterior longitudinal ligament of the spine, myocardial ischemia, joint calcification, heterotropic ossification of traumatized muscle, angioid streaks, diabetes mellitus type II, cardiovascular disorder, or atherosclerosis. The subject is generally a human, but may also be any other suitable mammal or non-mammal.

Diseases or disorders characterized by tissue calcification, particularly soft tissue calcification, include, but are not limited to, generalized arterial calcification of infancy (GACI), pseudoxanthoma elasticum (PXE), Arterial Calcification Due to Deficiency of CD73 (ACDC), vascular calcification in chronic kidney disease (VCCKD), insulin resistance, hypophosphatemic rickets, ossification of the posterior longitudinal ligament of the spine, myocardial ischemia, joint calcification, heterotropic ossification of traumatized muscle, and angioid streaks. Also treatment of conditions that can be improved by reducing and/or eliminating one or more calcification structures and/or preventing calcification structures from forming in a subject, are within the scope of the present invention. Such conditions include, without limitation, Ehlers-Danlos syndrome, arteriosclerosis obliterans, venous calcifications, crystal deposition disorders, calcification resulting from neurological disorders, calcinosis universalis, calcinosis circumscripta, scleroderma, dermatomyositis, systemic lupus erythematosus, hyperparathyroidism, neoplasms, milk-alkali syndrome, hypervitaminosis D, and tumoral calcinosis, Generally, the dosage of PPi administered to a subject in need thereof will vary depending upon age, health and weight of the subject, frequency of treatment, and the like. For example, a dosage of PPi may be between about 0.1 mg per kg of body weight and about 1 g per kg of body weight, e.g., between about 0.5 mg per kg of body weight and about 500 mg per kg of body weight, or between about 1 mg per kg of body weight and about 300 mg per kg of body weight, or between about 10 mg per kg of body weight and about 200 mg per kg of body weight, or between about 20 mg per kg of body weight and about 150 mg per kg of body weight. Precise dosage and frequency of administration can be determined by a physician skilled in the art. The skilled physician will readily appreciate that certain factors may influence the dosage required to effectively treat a subject, including, but not limited to, the severity of the disease, previous treatments, the general health and/or age of the subject, and other diseases present in the subject.

The dosage of PPi may be in the form of a unit-dosage comprising all of the therapeutically effective amount, or may be contained in multiple dosage forms. The PPi may be administered once daily, twice daily, or the like. It will be appreciated that the effective dosage of PPi used for the treatment taught herein may increase or decrease over the course of the treatment.

The oral PPi may be administered to a subject for a period of time determined by a skilled physician. In one embodiment, e.g., for certain hereditary calcification disorders, the period of time will be the remainder of the subject's life span.

In one embodiment, the subject is an infant. The subject may be between 1 month and 24 months in age, less than 1 year of age, less than 2 years of age, less than 3 years of age, less than 4 years of age, less than 5 years of age, or less than 6 years of age.

In an embodiment, the level of blood PPi in a subject prior to treatment is less than about 80%, such as less than about 70%, less than about 60%, less than about 50%, less than about 40%, less than about 30%, less than about 25%, less than about 20%, less than about 15%, less than about 10%, less than about 5%, less than about 3%, less than about 2% or less than about 1% of normal levels of PPi observed in a healthy human subject. In an embodiment, a subject shows no measurable level of blood PPi prior to treatment.

In an embodiment, the PPi may be administered in conjunction with a pharmaceutically acceptable carrier, diluent, or excipient. As according to the invention the PPi is administered orally, it may be presented in any form suitable for such administration, e.g. in the form of tablets, capsules, powders, syrups or solutions. In one embodiment, the PPi is administered in the form of a solid pharmaceutical entity, suitably as a tablet or a capsule. Methods for the preparation of solid pharmaceutical compositions or preparations are well known in the art. Thus, tablets may be prepared by mixing the active ingredient with conventional adjuvants, fillers and diluents and subsequently compressing the mixture in a suitable tableting machine. Examples of adjuvants, fillers and diluents comprise cornstarch, lactose, talcum, magnesium stearate, gelatine, gums, and the like. Typical fillers are selected from lactose, mannitol, sorbitol, cellulose and microcrystalline cellulose. Any other adjuvant or additive such as colourings, aroma, preservatives, etc, may also be used provided that they are compatible with the active ingredient PPi.

In an embodiment, the PPi may be included in a food or food supplement product, e.g., a sweet or chewing gum, or the like.

The oral PPi may be administered alone or in combination with other agents. The PPi may be administered before, after, or concurrently with such other agents or can be co-administered with other known therapies.

In an embodiment, the present disclosure pertains to a method for preventing and/or reducing tissue calcification, particularly soft tissue calcification, and/or diseases or disorders characterized by low plasma PPi levels, in a subject in need thereof. The method is based on the surprising finding that oral PPi can be administered to a subject that has low plasma PPi levels to cause a transient increase in plasma PPi in the subject, which can inhibit tissue calcification, particularly soft tissue calcification, in the subject. Since the increase in plasma PPi is transient, therapy can be tailored to inhibit undesirable or pathological tissue calcification, without inhibiting bone calcification or inducing osteomalacia.

In an embodiment, the disclosure relates to a method for reducing tissue calcification (e.g. soft tissue calcification) in a subject in need thereof, by administering to the subject one or more doses of PPi. Each dose may contain an amount of PPi that is sufficient to achieve a transient increase in plasma PPi in the subject.

In an embodiment, the PPi level in the blood returns to its base level within about 24 hours, such as within 18 hours, within 12 hours, within 6 hours, or within 4 hours, after administration of the dose. The time period between the administration of each dose may vary. For example, oral PPi may be administered twice a day, daily, once every two days, once every three days, once every fours days, or the like.

In an embodiment, each dose of oral PPi that is administered to the subject contains an amount of PPi sufficient to achieve a transient increase in plasma PPi level, which may have a peak that is above 200%, or that is between about 40% and about 200%, such as between about 50% and 150%, between about 60% and about 125%, between about 70% and about 100%, between about 80% and about 90%, of the plasma PPi level observed in healthy subjects.

In an embodiment, the transient increase in plasma PPi level after oral administration of PPi is maintained for at least about 10 minutes, 15 minutes, 30 minutes, 1 hour, or the like. Further, it is preferred that the plasma PPi level returns to its base level within about 24 hours, such as within about 18 hours, 12 hours, 6 hours, 5 hours, 4 hours, 3 hours, 2 hours, 1 hour or less after administration of the dose.

The low plasma PPi levels in a subject prior to treatment may be about 50% or less, 40% or less, 30% or less, 20% or less, or 10% or less, of the plasma PPi levels observed in a healthy subject.

Tissue calcification is a progressive process, and individuals born with congenital deficiencies leading to low plasma PPi levels may not show tissue calcification for several years. In order to reduce or minimize calcification in such subjects, therapy should be initiated as early as possible, preferably even before tissue calcification is noticed. It was found by the present inventors that administration of PPi to a pregnant mammal and PPi therapy of the baby after birth reduced or minimized calcification in the fetus and/or baby.

In subjects with low plasma PPi levels which do not have congenital deficiencies, therapy should begin as soon as practicable; i.e. soon after the diagnosis of the conditions, such as CKD or ESRD.

The invention is further exemplified by the following examples, which are intended for illustrative purpose only, and which are not intended to be construed as limiting the invention in any manner.

The calcium content of the tissue blocks of the hair capsules was determined (panel A). Panels B, C and D show typical alizarin red stained sections of an animal of each group. Panel E: delay of the day of onset of the tiptoe walking phenotype in pups kept on water or on 10 mM PPi either during pregnancy, breast feeding and after weaning or only during the pregnancy, or during breast feeding and after weaning, but not during the pregnancy.

Figure 4:
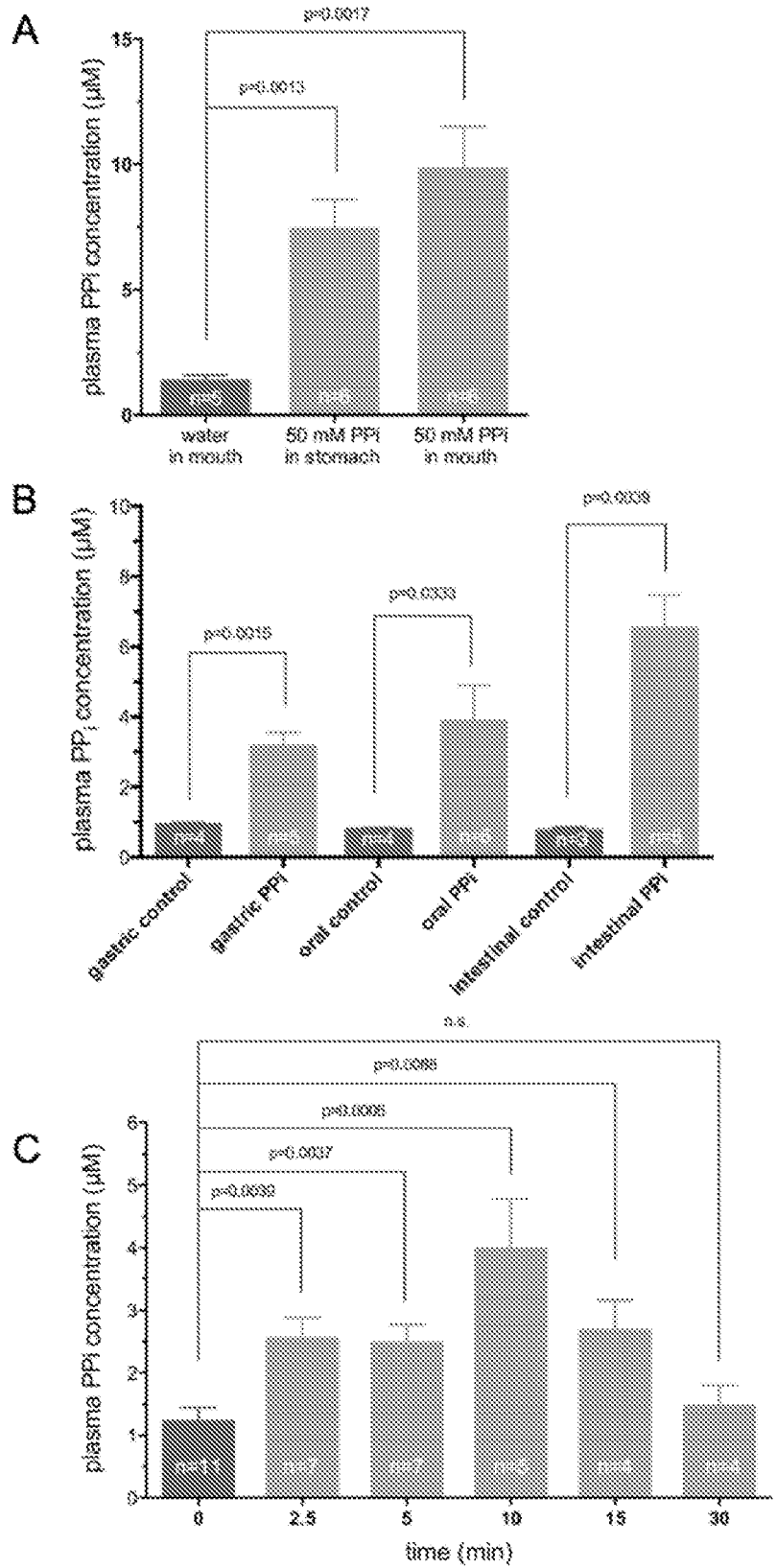

FIG. 4 shows uptake of PPi from drinking water in mice. A: Uptake from the oral cavity and from the stomach by continuous delivery of 50 mM PPi to Abcc6$^{-/-}$ mice without ligation. Mice were anesthetized and paper-pads placed into the mouth; 30 ul aliquots of 50 mM PPi were given by 10 minute-intervals for one hour. Blood was collected for PPi assay at the end of PPi administration, at 60 min. 50 mM PPi was provided in 30 ul aliquots directly into the stomach by a gavage into anesthetized Abcc6$^{-/-}$ mice for 60 minutes in the intervals described above and blood was collected for PPi assay at 60 minutes.

B: Uptake from the oral cavity, from the stomach and from the intestine of C57/Bl6 mice after ligating the esophagus and applied oral delivery of 100 ul 50 mM PPi or the pylorus followed by stomach delivery of 200 ul 50 mM PPi and then ligation the esophagus, or injecting 200 ul 50 mM PPi into the intestine after ligation of the pylorus. In each experiment blood was collected after 15 min and PPi concentrations were determined.

C: Plasma PPi concentrations after delivery of 200 ul of 50 mM PPi by gavage into the stomach of C57/Bl6 mice.

Figure 5:
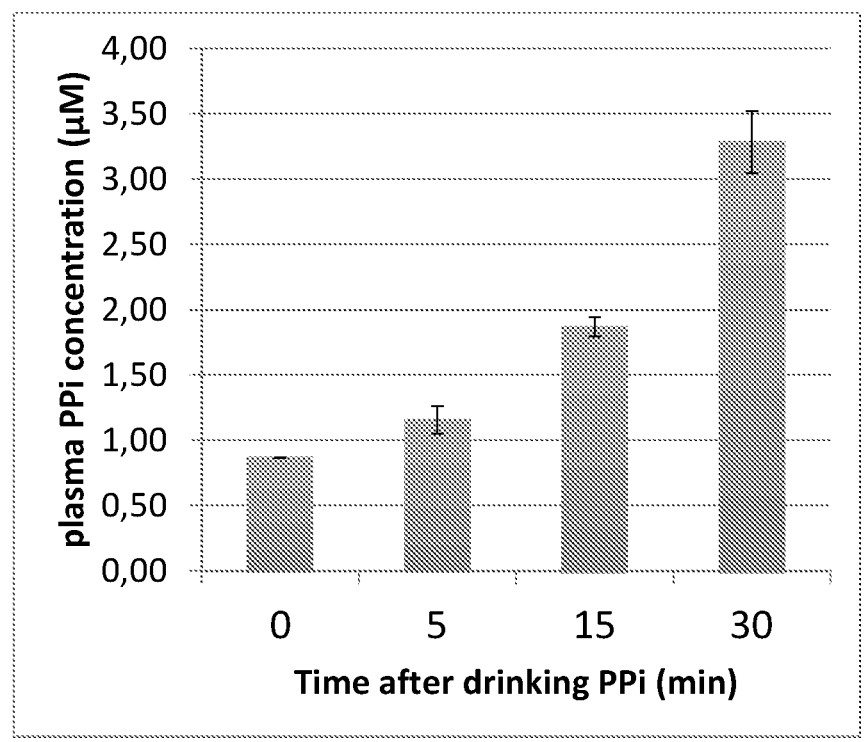

FIG. 5 shows uptake of PPi from drinking water in a human volunteer.

EXAMPLES

Animals and Animal Studies

C57BL/6J mice, designated as wild type were derived from mice purchased from The Jacksons Laboratories. Abcc6$^{-/-}$ mice were generated on 129/Ola background and backcrossed into a C57BL/6J>10 time[1]. Ttw mice were obtained from Ttw$^{+/-}$ mating and each offspring was genotyped. C3H/He mice were purchased from Harlan (The Netherlands). Both male and female, age-matched Abcc6$^{-/-}$, Ttw, C3H/He and wild type mice were used.

All animals were housed in approved animal facilities at the Research Center for Natural Sciences, Hungarian Academy of Sciences. Mice were kept under routine laboratory conditions with 12 hour light-dark cycle with ad libitum access to water and chow. The RCNS, Hungarian Academy of Sciences Institutional Animal Care and Use Committees approved this study. Experiments have been conducted according to national guidelines. Cryo injury was performed and tissue calcium content was determined as described by Brampton, et al. ((2014) *Am J Pathol.* 184, 159-70). Calcification of the vibrissae was studied by histochemistry following the method described Klement, et al. ((2005) *Mol Cell Biol.* 25, 8299-310. The number of calcified vibrissae (hair capsules) was counted independently and the onset of tiptoe walking phenotype was determined by two investigators in a blinded fashion.

Pyrophosphate Measurements

Determination of PPi concentration in plasma was performed as described by Jansen et al ((2014) *Arterioscler Thromb Vasc Biol.* 34, 1985-9). Sodium pyrophosphate tetrabasic decahydrate (BioXtra quality) was purchased from Sigma.

Statistical Analysis

Data were compared by the Student t test. Values are expressed as mean+/−standard error of the mean (SEM). A p value<0.05 was considered statistically significant. Animal numbers used for individual set of data varied and is shown on the figures.

Results

Abcc6$^{-/-}$ mice faithfully recapitulate human PXE, with calcifying lesions found in skin, eyes and blood vessels. A drawback of the Abcc6$^{-/-}$ mice is the relatively late onset of the first lesions, making this model less convenient for rapid screening of new treatments. However, cryo-injury applied to the heart results in a calcified lesion within 3-6 days, a phenomenon fully dependent on the absence of Abcc6. As daily intraperitoneal (IP) PPi injections prevented calcification in several animal disease models, IP delivery (6 mg PPi/kg body weight for 7 days) in Abcc6$^{-/-}$ mice was tested.

Indeed, PPi injections reduced the cardiac calcification (ICC) induced by cryo-injury (data not shown).

Figure 1:
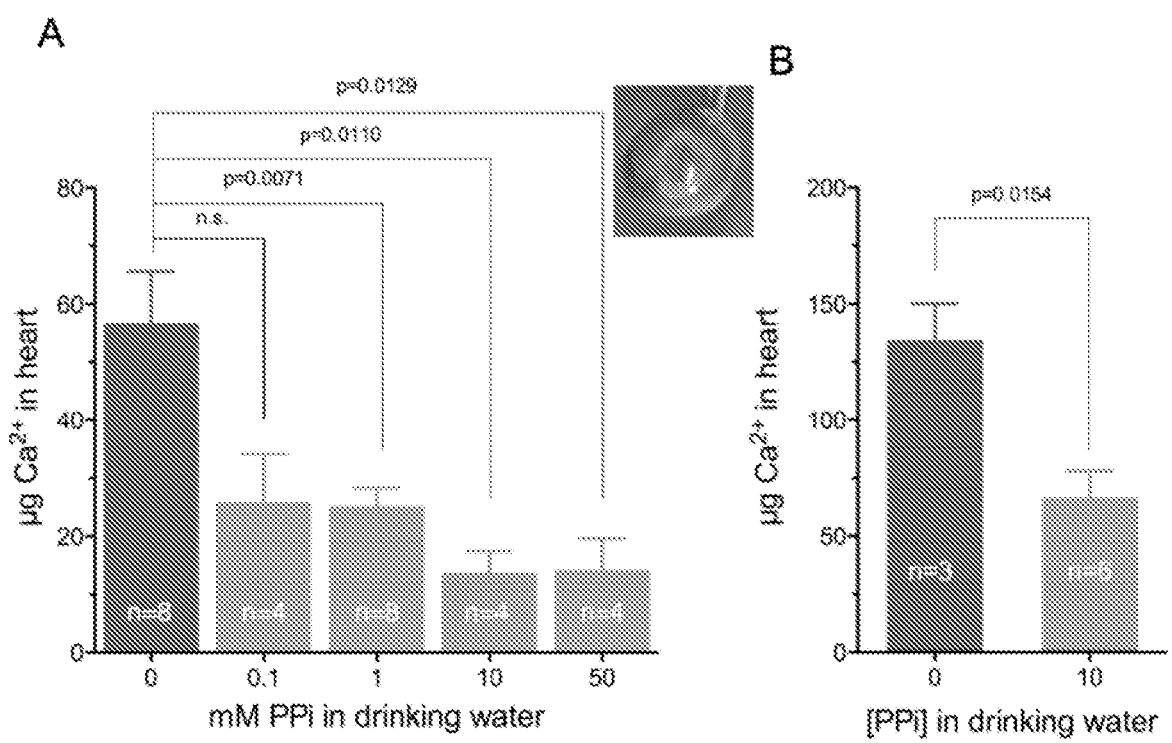
FIG. 1 shows that oral PPi attenuates induced cardiac calcification in Abcc6$^{-/-}$ mice. PPi was provided in various concentrations (0.1-50 mM) in the drinking water to Abcc6$^{-/-}$ (A) or to C3H/He (B) mice (in which an alternative splice variant in Abcc6 leads to protein deficiency) a day before the cryo injury and continued for four days when the animals were sacrificed. The calcium content of heart tissue was determined. The insert shows calcification of the heart of Abcc6$^{-/-}$ mice four days after cryo-injury.
Figure 2:
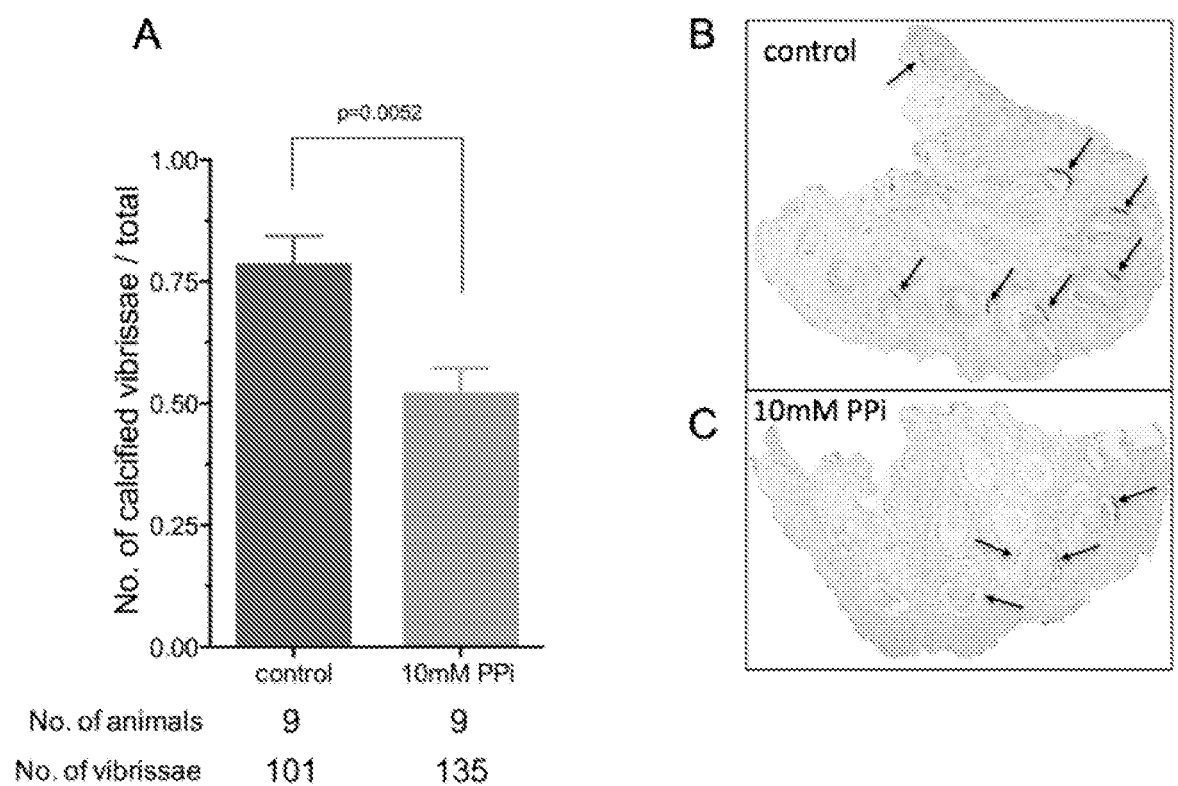
FIG. 2 shows that oral PPi attenuates the spontaneous hair capsule calcification of vibrissae in Abcc6$^{-/-}$ mice. Abcc6$^{-/-}$ mice were kept on 10 mM PPi (in drinking water) starting 3 weeks after weaning until they were 22 weeks old. The control group was drinking tap water. Tissue blocks with the hair capsules were removed, paraffin-embedded, sectioned and stained with alizarin red for calcium deposits. The extent of calcification was expressed as the ratio of the number of calcifying capsules per total number of capsules (A). Panels B and C show typical alizarin red stained sections of an animal of the control group and that of the 10 mM PPi group, respectively.

It was then tested whether orally administered PPi also inhibited the calcification seen in the ICC model. It was found that PPi provided via the drinking water potently inhibited ICC. The extent of calcification inhibition was dose-dependent, with maximal inhibition seen at a PPi concentration of 10 mM (FIG. 1). Next, it was tested whether the spontaneous ectopic calcification seen in $Abcc6^{-/-}$ mice could also be attenuated by PPi administration via the drinking water. A peculiar phenotype seen in $Abcc6^{-/-}$ mice is the gradual calcification of the tissue surrounding the vibrissae. Therefore, the effect of oral PPi on the calcification of the dermal sheet surrounding the vibrissae was determined. Just after weaning $Abcc6^{-/-}$ mice were put on PPi-containing drinking water (10 mM) for a period of 19 weeks. Then the effect of the PPi-containing drinking water on the number of calcified vibrissae was determined. As can be seen in FIG. 2, PPi provided via the drinking water also potently inhibited the spontaneous calcification seen in $Abcc6^{-/-}$ mice.

Tiptoe walking (ttw) mice have an inactivating mutation in Enpp1 and represent a model for GACI. Due to the complete absence of Enpp1, these mice have extremely low plasma PPi levels and develop extensive calcifications in the skin, blood vessels and joints shortly after birth. Just like $Abcc6^{-/-}$ mice, the ttw mice show extensive calcification of the dermal sheet surrounding the vibrissae, although in these animals this phenotype shows up much earlier than in mice lacking Abcc6. It was tested whether supplementation of PPi via the drinking water also effectively attenuated this ectopic calcification in the ttw mice.

Figure 3:
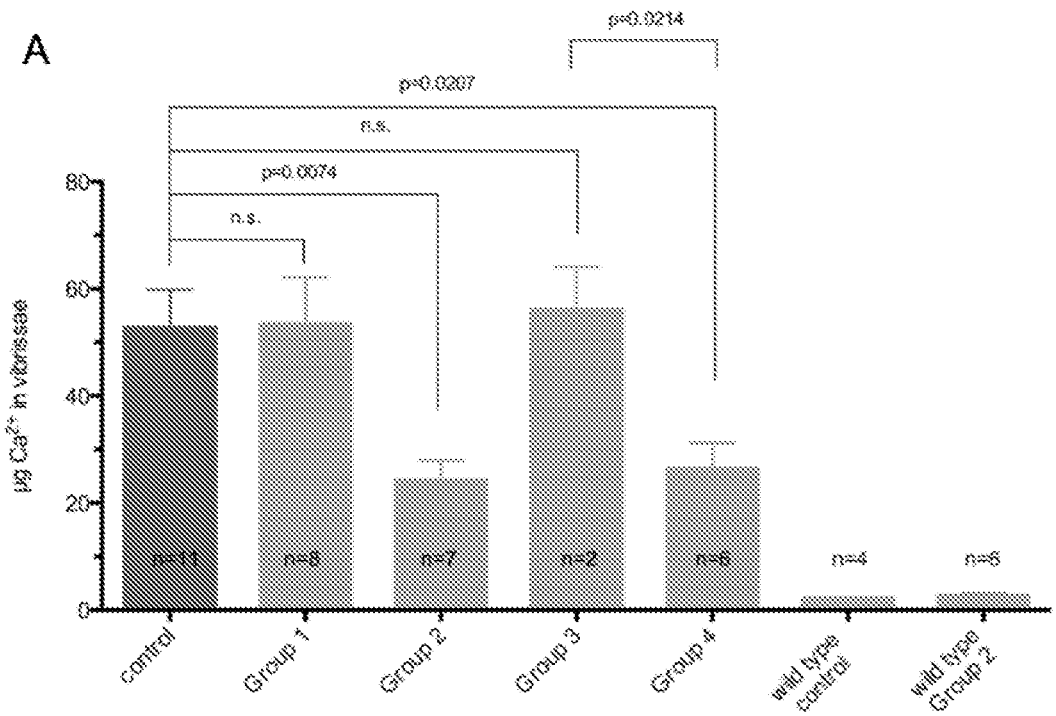
FIG. 3 shows that prenatal PPi treatment of the Enpp1$^{-/-}$ mice attenuates the spontaneous hair capsule calcification of the vibrissae and delays the tiptoe walking phenotype. The mother and the pups were kept on tap water until the pups were 30 days old ("control"); Group 1: as the control group, but for 9 days on 10 mM PPi solution after weaning at 21 days. Group 2: the mothers and the pups were kept on 10 mM PPi during pregnancy, breast feeding and for 9 days after weaning. Group 3: the mothers and the pups were kept on 10 mM PPi during breast feeding and for 9 days after weaning. Group 4: the mothers were kept on 10 mM PPi during pregnancy. Wild type controls are also shown.
Figure 3:
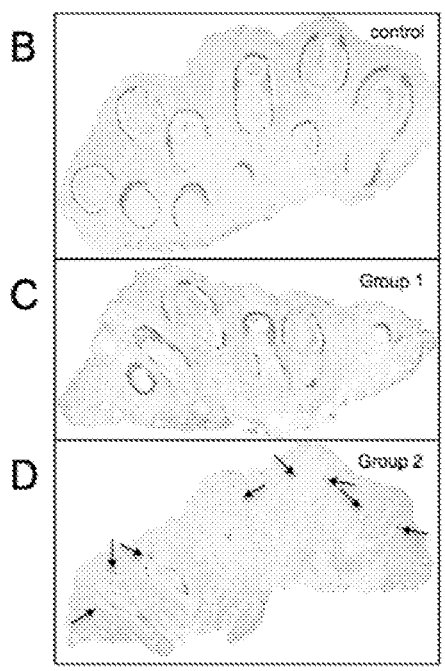

When PPi was given orally during pregnancy and lactation and afterwards the PPi treatment of the pups was continued, the calcification of the dermal sheet surrounding the vibrissae was greatly reduced (see FIG. 3). To determine when PPi treatment was most effective, the effect of PPi was analyzed separately during pregnancy, lactation and after weaning. When we only treated the ttw pups after weaning, the amount of calcification was no different from the control-treated group. PPi provided during lactation had no significant impact on calcification either. However, the most remarkable finding of these experiments was that the effect of PPi was maximal if administered during pregnancy. The same was true when the tiptoe walking phenotype (due to joint calcification) was determined (FIG. 3), which was delayed by four days in the "PPi during pregnancy" group.

An explanation for these results is that microcrystals have already been formed in the control-treated group before birth. Without wishing to be bound by theory, it is hypothesized that these microcrystals might be mostly absent in ttw pups from mothers on PPi during pregnancy and may therefore not be available to accelerate the calcification process after weaning. Our data clearly demonstrate that orally administered PPi attenuates ectopic calcification.

Uptake of PPi from the Oral Cavity and from the Stomach in Mice

Mice were anesthetized and paper-pads placed into the mouth; 30 ul aliquots of 50 mM PPi were given by 10 minute-intervals for one hour. Blood was collected for PPi assay at the end of PPi administration, at 60 min. Alternatively, 50 mM PPi was provided in 30 ul aliquots directly into the stomach by a gavage into anesthetized Abcc6−/− mice for 60 minutes in the intervals described above and blood was collected for PPi assay at 60 minutes. It was found that PPi was taken up from both the oral cavity and the stomach (FIG. 4).

Uptake of PPi into Plasma in Human

A human volunteer drank 300 ml 100 mM $Na_4PPi$ pH8, and plasma PPi concentrations were measured in time. It was shown that orally administered PPi was taken up to provide increase plasma PPi levels (FIG. 5).

The invention claimed is:

1. A method for treating and/or ameliorating generalized arterial calcification of infancy (GACI) or pseudoxanthoma elasticum (PXE), the method comprising the step of:
    administering to a subject in need thereof a therapeutically effective amount of inorganic pyrophosphate (PPi),
    wherein said inorganic pyrophosphate is administered in oral form and
    wherein the inorganic pyrophosphate is sufficient to achieve a transient increase in plasma PPi level in the subject.

2. The method according to claim 1, wherein the transient increase in plasma PPi level is characterized by a PPi level that is at least about 40% of the plasma PPi level in a healthy subject.

3. The method according to claim 1, wherein the transient increase in plasma PPi level is maintained for at least about 15 minutes.

4. The method according to claim 1, wherein the treating is slows the progression of the GACI or PXE.

\* \* \* \* \*